Dec. 30, 1947. L. W. SHERWOOD Plant Pat. 773
AVOCADO TREE
Filed Jan. 9, 1947
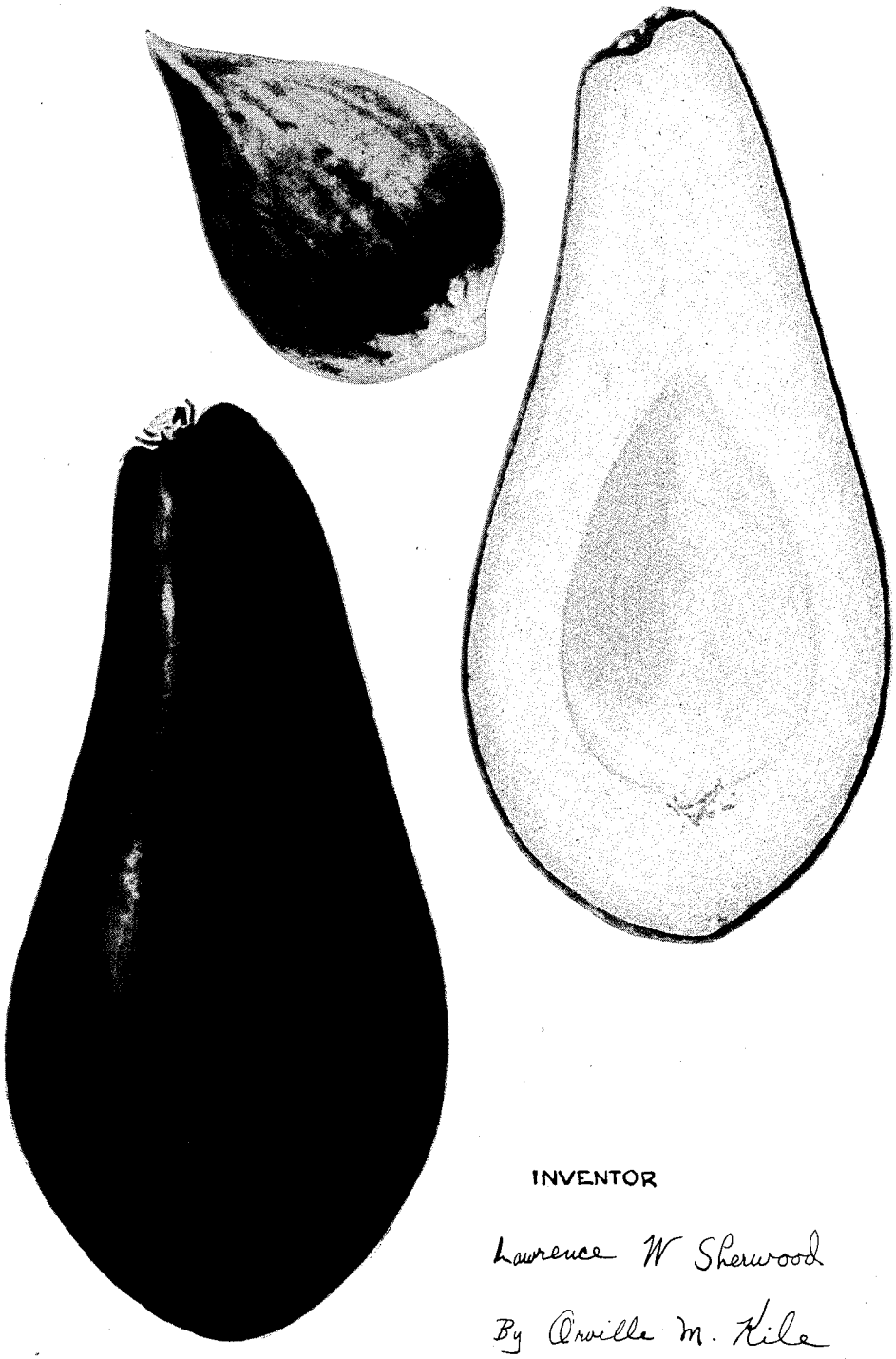
INVENTOR
Lawrence W Sherwood
By Orville M. Kile
PLANT PATENT AGENT Patented Dec. 30, 1947

Plant Pat. 773

UNITED STATES PATENT OFFICE

773

AVOCADO TREE

Lawrence W. Sherwood, Fullerton, Calif.

Application January 9, 1947, Serial No. 721,055

1 Claim. (Cl. 47—62)

My present discovery relates to a new and distinct variety of avocado tree of the Mexican type which is an improvement over previously known varieties of this type and which produces readily marketable fruit of superior quality.

This new variety originated as a chance seedling among a number of trees grown from seeds of a Mexican seedling of unknown parentage which was planted about 40 years ago. It has particularly outstanding foliage and tree structure. The tree is a very prolific bearer, consistently producing a large crop of high quality fruit each year.

The oil content of the fruit is unusually high for this type of avocado, and the flesh has a nutty flavor and buttery consistency. The seed is small and a large portion of the flesh is in the relatively long neck, thus providing a high percentage of edible content. Outer appearance of the fruit is much like that of a small eggplant, both in color and shape. The seed is loose in its cavity when ripe and is easily removed, and the flesh is easily removed from the thick skin with a spoon.

The accompanying illustrations show a side view and a cross section view of the fruit of my new avocado variety, and a view of the seed removed therefrom, in approximately true colors and somewhat enlarged in size in the original paintings.

Asexual reproduction of this variety by budding has shown the above characteristics to be firmly fixed in the variety.

Following is a detailed description of the tree and fruit of this new variety, color means referring to the ordinary dictionary definitions of the terms.

*The tree*

Growth habits: More upright than spreading. Numerous limbs, branches and foliage sufficiently cover the fruit to protect it from the hot sun in its growing season.

Bearing habits: Very prolific bearer, early and consistently producing a heavy crop of high quality fruit each year.

Hardiness: In the locations in which I have grown this new variety it seems quite hardy and unusually resistant to frosts that damage most avocado varieties.

Maturity: My original tree fruited at five years from the time of planting the seed. Budded trees come into bearing at an early age—much earlier than most varieties known to me.

Blossoming: This variety blossoms 1½ to 2 months before Fuerte and has a season of about the same length as Fuerte between its blossoming and fruit ripening.

Fruit placement: Fruit is very evenly distributed over the tree, mostly in single fruit. It occurs sufficiently back from the terminal ends of branches to be well protected by the foliage.

Ripening date: Ripens between principal summer varieties and principal winter varieties; approximately September 15th in Southern California. This brings it at a season where avocados of good quality are scarce.

Foliage:

*Quantity.*—Abundant.

*Color.*—Rich bright medium green; very dense without open uncolored spots.

*Size.*—Average 3½ inches wide at the broadest point, and 8½ inches long.

*Shape.*—Long and narrow. More narrow at stem end than other known varieties, and extremely pointed at apex.

*Texture and veining.*—Smooth. Veins prominent and fairly abundant.

*Distribution.*—Leaves do not occur in bunches but are well distributed over the tree, thus shielding the fruit.

*The fruit*

Size: Length about 4½ inches. Cross section maximum width is approximately 2½ inches. Stem end about 1 inch in width. This is a very desirable size for marketing.

Weight: From 8 to 12 ounces.

Shape: Evenly tapered, with very long fleshy neck portion.

Skin:

*Color.*—When in its prime, skin is bright purple with small brown spots. Color is very similar to that of an eggplant.

*Aspect.*—Smooth and glossy.

*Texture.*—Not tough and heavy but thick enough to protect fruit well when shipped and to enable the flesh to be easily separated from it with a spoon.

Flesh:

*Color.*—Pale yellow, with edge of bright green just under the skin.

*Flavor.*—Mild and nutty. Similar to that of Fuerte.

*Texture.*—Buttery. Free from coarse fiber.

*Oil content.*—Very high. Almost as rich as Fuerte.

Seed:

*Shape.*—Shaped like a long top with acute apex.

*Size.*—Approximately 1½ inches across at larger end and 1¾ inches in length. Small for size of fruit, proportion of flesh being greater than for the average avocado of its weight.

*Separability.*—Loose in cavity when ripe. Outer covering separates easily.

Having thus disclosed my discovery, I claim: The new and distinct variety of avocado tree of the Mexican type, substantially as herein shown and described, distinguished as to novelty by its consistently prolific production of high quality fruit each year; its early maturity; its early fall ripening season; its hardiness; its long narrow leaves; the protected position of its fruit on the tree; and its fruit characterized by bright purple color of the skin, convenient marketable size, skin thick enough to protect fruit well in shipping; mild rich buttery flesh with high oil content, and proportionately small seed with pointed apex which together with the long neck results in a high proportion of flesh to total weight.

LAWRENCE W. SHERWOOD.